United States Patent
Fanger et al.

(10) Patent No.: US 7,141,074 B2
(45) Date of Patent: Nov. 28, 2006

(54) VARIABLE DEPTH DRILL WITH SELF-CENTERING SLEEVE

(75) Inventors: Jonathan Fanger, Fall River, MA (US); Eric D. Kolb, Quincy, MA (US); Richard Fessler, Winnetka, IL (US)

(73) Assignee: Depuy Spine, Inc., Raynham, MA (US)

( * ) Notice: Subject to any disclaimer, the term of this patent is extended or adjusted under 35 U.S.C. 154(b) by 319 days.

(21) Appl. No.: 10/665,717

(22) Filed: Sep. 17, 2003

(65) Prior Publication Data
US 2005/0059975 A1    Mar. 17, 2005

(51) Int. Cl.
*A61B 17/00* (2006.01)
(52) U.S. Cl. ...................................................... 623/80
(58) Field of Classification Search ................. 606/80, 606/96, 79, 86, 97, 98; 408/112, 119, 202, 408/241 G, 241 S, 6
See application file for complete search history.

(56) References Cited

U.S. PATENT DOCUMENTS

| | | | |
|---|---|---|---|
| 854,956 A * | 5/1907 | Martin ......................... | 606/80 |
| 1,831,813 A * | 11/1931 | Axel ............................ | 408/81 |
| 2,338,765 A * | 1/1944 | Hartman ...................... | 408/81 |
| 2,798,520 A * | 7/1957 | Maskulka et al. ....... | 408/241 G |
| 3,128,768 A * | 4/1964 | Mikelis ....................... | 606/180 |
| 3,320,832 A * | 5/1967 | Jensen ......................... | 408/112 |
| 3,336,611 A * | 8/1967 | Schepp ............................ | 7/158 |
| 3,540,322 A * | 11/1970 | Swanson ..................... | 408/112 |
| 4,027,992 A * | 6/1977 | Mackey et al. ................ | 408/97 |
| 4,039,266 A * | 8/1977 | O'Connell .................. | 408/202 |
| 4,138,200 A * | 2/1979 | Nazarenus .............. | 408/241 S |
| 4,168,131 A * | 9/1979 | Hill ............................. | 408/1 R |
| 4,273,117 A * | 6/1981 | Neuhauser .................... | 606/80 |
| 4,502,475 A | 3/1985 | Weigle et al. | |
| 4,586,846 A * | 5/1986 | Kellison ......................... | 404/6 |
| 4,686,972 A | 8/1987 | Kurland | |
| 4,710,075 A * | 12/1987 | Davison ..................... | 408/202 |
| 4,969,781 A * | 11/1990 | Fahrner et al. ............... | 408/79 |
| 5,197,967 A * | 3/1993 | Wilson ......................... | 606/79 |
| 5,303,694 A | 4/1994 | Mikhail | |
| 5,423,826 A | 6/1995 | Coates et al. | |
| 5,558,622 A | 9/1996 | Greenberg | |
| 5,649,793 A * | 7/1997 | Ericksen et al. .............. | 408/81 |
| 5,669,915 A * | 9/1997 | Caspar et al. ................. | 606/96 |

(Continued)

FOREIGN PATENT DOCUMENTS

DE    3800482 A1    7/1989

(Continued)

*Primary Examiner*—Alvin J. Stewart
(74) *Attorney, Agent, or Firm*—Nutter, McClennen & Fish LLP (57) ABSTRACT

A surgical drill assembly is provided that includes an elongate shaft having a proximal end adapted to mate to a driver mechanism, and a distal end having a bone preparation element formed thereon. An elongate, hollow sleeve is coupled to, but slidably disposed around at least a portion of the elongate shaft. The hollow sleeve includes a stepped region that is positioned between proximal and distal portions such that the distal portion has an outer diameter that is less than an outer diameter of the stepped region to allow the distal portion to be disposed within a lumen in a drill guide, and the stepped region to abut the drill guide. In use, the elongate, hollow sleeve is effective to longitudinally align the elongate shaft therein during a surgical procedure. The elongate shaft can also optionally include a stop member that is effective to limit penetration depth of the bone preparation element with respect to the hollow sleeve.

25 Claims, 8 Drawing Sheets

U.S. PATENT DOCUMENTS

| | | | |
|---|---|---|---|
| 5,755,721 A | 5/1998 | Hearn | |
| 5,851,207 A | 12/1998 | Cesarone | |
| 5,881,613 A * | 3/1999 | Han | 81/429 |
| 5,890,897 A | 4/1999 | Kruger et al. | |
| 5,947,657 A * | 9/1999 | Lipohar et al. | 408/97 |
| 5,948,000 A * | 9/1999 | Larsen et al. | 606/232 |
| 6,110,178 A * | 8/2000 | Zech et al. | 606/96 |
| 6,162,225 A | 12/2000 | Gertzman et al. | |
| 6,162,226 A | 12/2000 | DeCarlo, Jr. et al. | |
| 6,235,034 B1 | 5/2001 | Bray | |
| 6,342,056 B1 | 1/2002 | Mac-Thiong et al. | |
| 6,342,057 B1 | 1/2002 | Brace et al. | |
| 6,379,364 B1 | 4/2002 | Brace et al. | |
| 6,416,518 B1 | 7/2002 | DeMayo | |
| 6,416,528 B1 | 7/2002 | Michelson | |
| 6,419,678 B1 | 7/2002 | Asfora | |
| 6,514,258 B1 | 2/2003 | Brown et al. | |
| 6,739,872 B1 * | 5/2004 | Turri | 433/75 |
| 6,951,562 B1 * | 10/2005 | Zwirnmann | 606/80 |
| 2003/0045880 A1 | 3/2003 | Michelson | |

FOREIGN PATENT DOCUMENTS

DE 3800482 A1 * 7/1989

* cited by examiner

VARIABLE DEPTH DRILL WITH SELF-CENTERING SLEEVE

FIELD OF THE INVENTION

This application relates to tools for use in spinal surgery, and in particular to a variable depth drill having a self-centering sleeve.

BACKGROUND OF THE INVENTION

Advancing age, as well as injury, can lead to changes in the bones, discs, joints, and ligaments of the spine, producing pain from nerve root compression. Under certain circumstances, alleviation of pain can be provided by performing a spinal fusion. This is a procedure that involves joining two or more adjacent vertebrae with a bone fixation device so that they no longer are able to move relative to each other. For a number of known reasons, bone fixation devices are useful for promoting proper healing of injured or damaged vertebral bone segments caused by trauma, tumor growth, or degenerative disc disease. The external fixation devices immobilize the injured bone segments to ensure the proper growth of new osseous tissue between the damaged segments. These types of external bone fixation devices often include internal bracing and instrumentation to stabilize the spinal column to facilitate the efficient healing of the damaged area without deformity or instability, while minimizing any immobilization and post-operative care of the patient.

One such device is a bone fixation plate that is used to immobilize adjacent skeletal parts such as bones. Typically, the fixation plate is a rigid metal or polymeric plate positioned to span bones or bone segments that require immobilization with respect to one another. The plate includes a plurality of screw openings, e.g., either holes or slots, for receiving bone screws that are used to fasten the plate to the respective bones so that the plate remains in contact with the bones and fixes them in a desired position. Bone plates can be useful in providing the mechanical support necessary to keep vertebral bodies in proper position and to bridge a weakened or diseased area, such as when a disc, vertebral body, or fragment has been removed.

Implantation of a spinal fixation plate can be difficult, as each plate must be properly aligned with the vertebral bodies, and holes for receiving the bone screws must be drilled into the vertebrae at precise angles. It is often necessary to use the bone plate as a drill guide for drilling and tapping the bone in preparation for receiving the bone screws. Such a procedure can be difficult, however, as the surgeon is required to securely and rigidly hold the bone plate against the vertebrae, obtain proper alignment, drill, tap, and finally set the bone screws. Thus, drill guide devices have been developed that facilitate plate implantation. These devices typically include one or more lumens extending therethrough that are configured to align with the screw bores formed in the fixation plate. Some drill guides serve only as a guide for a drill bit, and other drill guides having larger diameters that allow a screw to pass through them. While the later is preferred, as removal of the guide is not necessary for screw placement and the guide facilitates alignment of the screw, drill guides having lumens with a larger diameter for receiving a fastening screw cannot center a drill bit since the drill bit must have a diameter that is smaller than the diameter of the fastening screw head. Some secondary instruments have been provided to center the drill bit within the drill guide lumen, however the use of additional devices is undesirable as it complicates the surgical procedure.

Accordingly, there remains a need for a drill guide device that includes a self-centering sleeve for centering a drill bit with respect to a drill guide lumen. It is also desirable to provide a self-centering drill guide device that includes a variable depth-stop mechanism.

SUMMARY OF THE INVENTION

The present invention generally provides a surgical drill assembly that can be used to facilitate the placement of a spinal fixation plate along a patient's spinal column. In general, the surgical drill assembly includes an elongate shaft having a proximal end that is adapted to mate to a driver mechanism, and a distal end having a bone preparation element formed thereon. An elongate, hollow sleeve is coupled to, but slidably disposed around at least a portion of the elongate shaft. In an exemplary embodiment, the hollow sleeve includes a stepped region that is positioned between proximal and distal portions such that the distal portion of the hollow sleeve has an outer diameter that is less than an outer diameter of the stepped region. In use, the elongate, hollow sleeve is effective to longitudinally align the elongate shaft therein during a surgical procedure. More particularly, the distal portion of the hollow sleeve can be disposed within a lumen in a drill guide, and the stepped region will abut the drill guide. As a result, the sleeve aligns the bone preparation element with the lumen in the guide member, thus aligning the bone preparation element with a bore in a spinal fixation plate that is coupled to the guide member. This will provide the user with precise control over the entry angle of the bone preparation element into bone.

In one embodiment, the elongate shaft can be biased with respect to the elongate, hollow sleeve to prevent the shaft from interfering with insertion of the sleeve into a lumen in a guide device. The biasing force is preferably adapted such that a force is necessary to overcome the biasing force to cause the elongate shaft to move in a distal direction with respect to the elongate, hollow sleeve. The biasing force can be created by a biasing member, such as a spring, that is disposed within at least a portion of the elongate, hollow sleeve to bias the elongate shaft in a proximal direction such that a force greater than a biasing force created by the biasing member is required to move the elongate shaft in a distal direction with respect to the elongate, hollow sleeve. The biasing member preferably acts on a flange that is formed around the elongate shaft, such that distal movement of the elongate shaft will cause the flange to abut and compress the biasing member. The device can also optionally include a pin extending through a sidewall of the hollow sleeve that is adapted to abut the flange to prevent removal of the elongate shaft from within the hollow sleeve. In an alternative embodiment, an engagement member, such as a ball and detent, can be formed on and disposed between the elongate shaft and the hollow sleeve such that the engagement member is effective to maintain the hollow sleeve in a predetermined position with respect to the elongate shaft.

The present invention also provides a stop member that can be disposed around a proximal portion of the elongate shaft and that is effective to limit penetration of the distal end of the elongate shaft into bone. The stop member can include a distal surface that acts on a proximal surface of the hollow sleeve to limit penetration of the distal end of the elongate shaft into bone. In an exemplary embodiment, the stop member can be in the form of a hollow tube that is disposed around the elongate shaft, and that is slidably adjustable between several fixed positions along a length of the elongate shaft. A push-button mechanism can be coupled to the stop member for engaging one of several detents formed in the elongate shaft to allow the position of the stop member along the length of the elongate shaft to be adjusted. In an exemplary embodiment, an inner surface of the hollow tube is threaded to mate with corresponding threads formed around at least a portion of the elongate shaft.

In another embodiment of the present invention, a surgical drill guide kit is provided. The kit can include a drill guide member that has at least one lumen formed therein that is adapted to align with at least one corresponding bore formed in a spinal fixation plate, an elongate shaft having a proximal end adapted to mate to a driver mechanism, and a distal end having a bone preparation element formed thereon, and an elongate, hollow sleeve that is disposed around at least a portion of the elongate shaft. The sleeve can include a distal portion that is adapted to fit within the at least one lumen in the drill guide member, and a proximal portion having at least a region with an outer diameter that is larger than an inner diameter of the at least one lumen. In use, the elongate, hollow sleeve is effective to longitudinally align the elongate shaft with the at least one lumen in the drill guide member and with at least one corresponding bore formed in a spinal fixation plate during a surgical procedure. The kit can also optionally include a spinal fixation plate having at least one bore formed therein, and at least one fastening element adapted to be disposed through the bore in the spinal fixation plate. The fastening element(s) preferably each have a proximal head and a distal, bone engaging portion. The proximal head has a diameter that is less than an inner diameter of the at least one lumen in the drill guide member, and that is greater than an inner diameter of the hollow, elongate sleeve. In an exemplary embodiment, the lumen(s) in the drill guide member each have a length that is substantially the same as a length of the distal portion of the hollow, elongate sleeve.

DETAILED DESCRIPTION OF THE INVENTION

Figure 1:
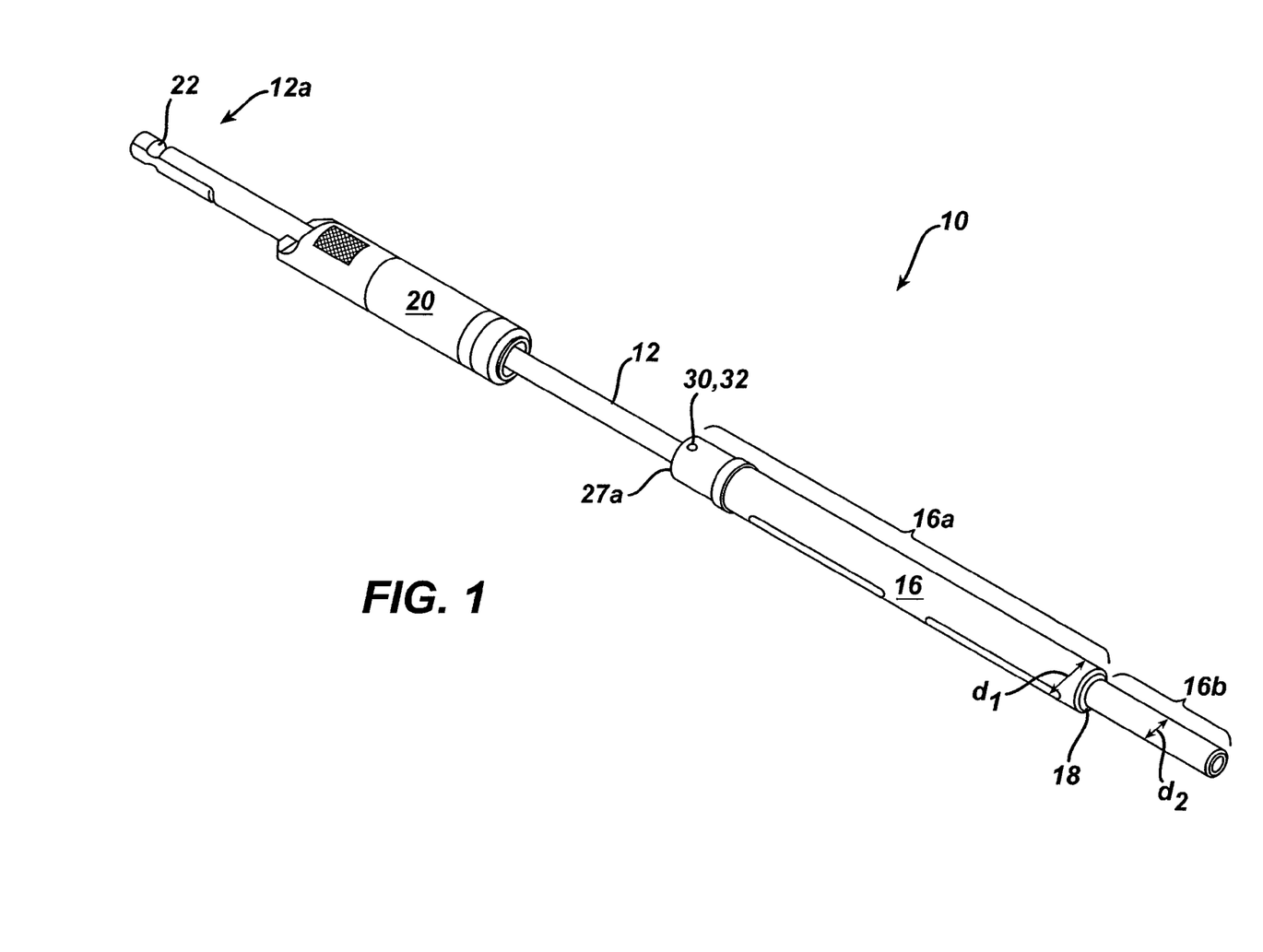
FIG. 1 is a perspective view of a surgical drill assembly according to one embodiment of the present invention.
Figure 2:
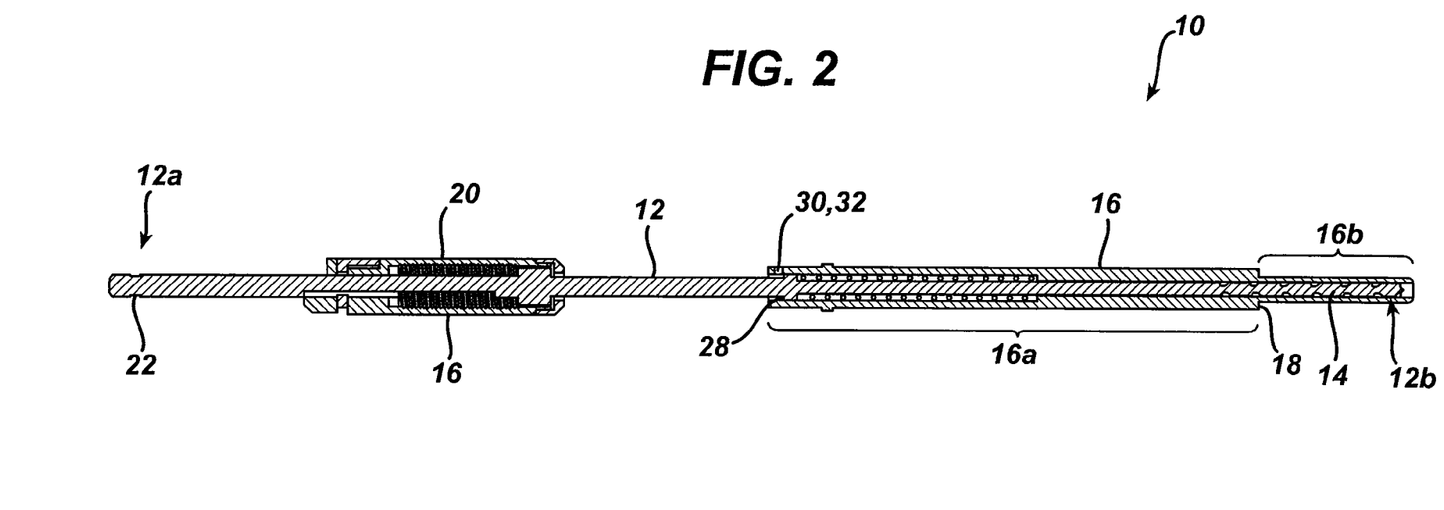
FIG. 2 is a cross-sectional view of the surgical drill assembly shown in FIG. 1.

As shown in FIGS. 1 and 2, the present invention generally provides a surgical drill assembly 10 that includes an elongate shaft 12 having a proximal end 12a that is adapted to mate to a driver mechanism, and a distal end 12b having a bone preparation element 14 formed thereon. An elongate, hollow sleeve 16 is coupled to, but slidably disposed around at least a portion of the elongate shaft 12. The hollow sleeve 16 includes a stepped region 18 that is positioned between proximal and distal portions 16a, 16b such that the distal portion 16b has an outer diameter $d_2$ that is less than an outer diameter $d_1$ of the stepped region. The device 10 can also optionally include a stop member 20 that is effective to the limit penetration depth of the bone preparation element 14 into bone.

In use, the stepped region 18 will allow the distal portion 16b of the sleeve 16 to be disposed within a lumen in a drill guide device, while the stepped region 18 abuts the drill guide device. Guide devices useful with the present invention will be discussed in more detail below, but in general a guide device will typically include at least one guide lumen or bore that is adapted to align with a corresponding bore on a spinal fixation plate. As a result of the stepped region 18, the elongate shaft 12 will be longitudinally aligned within the hollow sleeve 16, thereby aligning the elongate shaft 12 with the lumen in the guide device and with a corresponding screw bore formed in a spinal fixation plate that is coupled to and/or aligned with the guide device. After the bone is prepared using the surgical drill assembly 10, the assembly 10 can be easily removed from the drill guide device, allowing a fastening element to be inserted through the lumen in the guide device, since the guide lumen will necessarily have a larger inner diameter than an inner diameter of the hollow sleeve 16. The device 10 of the present invention offers several advantageous over prior art devices and techniques in that it reduces the number of instruments and procedural steps required during spinal surgery. In particular, since the device offers a self-centering bone-preparation instrument, it eliminates the need for additional centering mechanisms. The device, which can include a stop member, also offers the ability to control the penetration depth without the need for addition tools. One other advantage of the present invention is that the surgical drill assembly 10 allows for the use of a drill guide having relatively short guide lumens since the drill assembly 10 includes a sleeve 16 that is effective to extend the length of the guide lumen. A drill guide with short guide lumens provides greater visual and physical access to the surgical site.

Figures 3A, 3B:
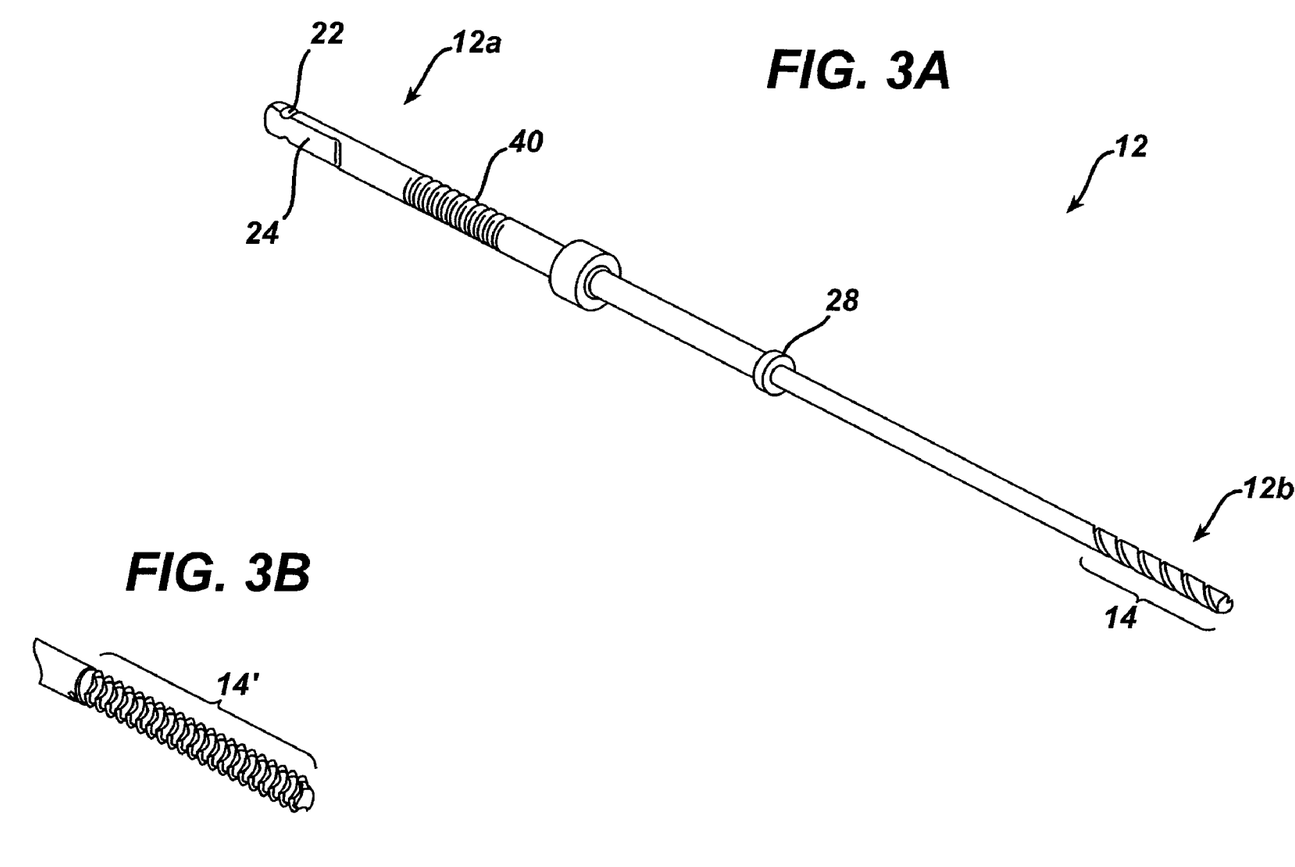
FIG. 3A is a perspective view of the elongate shaft of the surgical drill assembly shown in FIG. 1.
FIG. 3B is an alternative embodiment of the distal bone preparation portion of the elongate shaft shown in FIG. 3A.

The elongate shaft 12 of the surgical drill assembly 10 is shown in more detail in FIG. 3A, and it can have a variety of configurations. In general, the shaft 12 is preferably an elongate, cylindrical member having proximal and distal ends 12a, 12b. The proximal end 12a can include a mating element 22 formed thereon that is adapted to mate with a driver mechanism, which is preferably effective to rotate the shaft 12. The mating element 22 can have virtually any configuration, and the exact configuration will depend on the configuration of the driver mechanism. In an exemplary embodiment, the elongate shaft 12 is similar to a removable drill bit and the mating element 22 is in the form of an annular groove, as shown. The groove 22 allows the shaft 12 to be engaged by a driver mechanism. The shaft 12 can also include a flattened surface 24 that is effective to align the shaft 12 with the driver mechanism. A person skilled in the art will appreciate that virtually any mating technique can be used to mate the shaft 12 to a driver mechanism, and that a variety of driver mechanisms can be used with the surgical drill assembly 10 of the present invention.

The distal end 12b of the shaft 12 can also have a variety of configurations, but it preferably includes a bone preparation element 14 formed thereon, such as, for example, a drill, a tap, an awl, an auger, a reamer, a grinding member, and combinations thereof. As shown in FIG. 3A, the bone preparation element 14 is in the form of a drill. By way of non-limiting example, FIG. 3B illustrates another embodiment of a bone preparation element 14', which is in the form of a tap. A person skilled in the art will appreciate that the bone preparation element 14 can have virtually any configuration depending on the intended use.

The remaining features on the elongate shaft 12 will be discussed in more detail below.

Figure 4A:
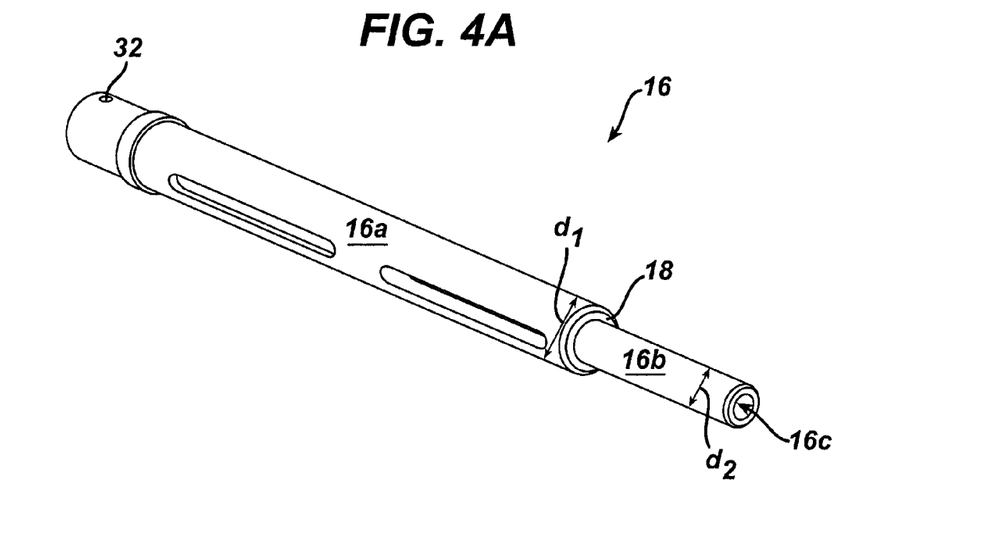
FIG. 4A is a perspective of the sleeve of the surgical drill assembly shown in FIG. 1.
Figure 4B:
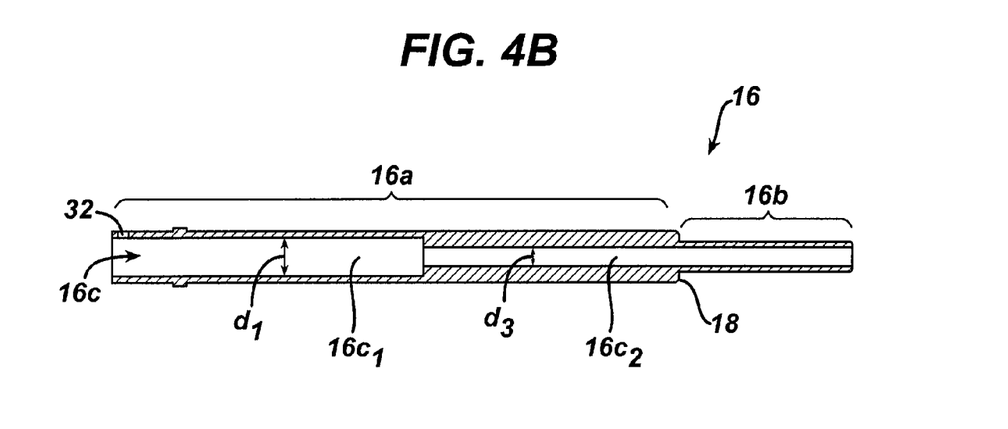
FIG. 4B is a cross-sectional view of the sleeve shown in FIG. 4A.

As previously stated, the surgical drill assembly 10 further includes a hollow sleeve 16 that is disposed around at least a portion of the elongate shaft 12. The hollow sleeve 16 can have a variety of configurations, but it should be effective to allow a portion of the sleeve 16 to be disposed within a lumen in a drill guide device and/or into a screw bore in a spinal fixation plate to center the elongate shaft 12 with respect to the lumen in the drill guide device and/or screw bore in the spinal fixation plate. FIGS. 4A and 4B illustrate an exemplary embodiment of a hollow sleeve 16 that has a generally cylindrical shape with an inner lumen 16c formed therein and extending through proximal and distal portions 16a, 16b thereof. A stepped region 18 is formed between the proximal and distal portions 16a, 16b such that the distal portion 16b has an outer diameter $d_2$ that is less than an outer diameter $d_1$ of the stepped region 18. This allows only the distal portion 16b to be disposed within a lumen in a drill guide device, while the stepped region 18 abuts the guide device. As shown, the stepped region 18 is formed from a stepped decrease in the outer diameter between the proximal and distal portions 16a, 16b. In particular, the proximal portion 16a has an outer diameter $d_1$ that is greater than an outer diameter $d_2$ of the distal portion 16b. The size of the outer diameters $d_1$, $d_2$ will vary depending on the size of the lumen of the guide device that is used in connection with the surgical drill guide 10, but each diameter $d_1$, $d_2$ should be configured so that the distal portion 16b has a diameter $d_2$ that is smaller than a diameter of a lumen formed in the guide device 10, and the proximal portion 16a has a diameter $d_1$ that is larger than the same lumen formed in the guide device 10. A person skilled in the art will appreciate that the stepped region 18 can have a variety of other configurations, and it can be formed from, for example, a flange that is disposed around the hollow sleeve 16.

The diameter of the inner lumen 16c of the hollow sleeve 16 can also vary, but at least a portion of the inner lumen 16c should be configured to center the elongate shaft 12 therein. More particularly, a portion of the inner lumen 16c should have a diameter $d_3$ that provides a clearance fit with the elongate shaft 12. The clearance fit can be, for example, a sliding fit that allows the elongate shaft 12 to move with respect to the sleeve 16, but that maintains a generally coaxial alignment between the shaft 12 and the sleeve 16. As shown in FIG. 4B, a distal portion $16c_2$ of the inner lumen 16c has a diameter $d_3$ that is adapted to provide a sliding fit with the elongate shaft 12. The remainder of the inner lumen 16c, e.g., the proximal portion $16c_1$ of the inner lumen 16c, has a diameter $d_4$ that is larger than the distal diameter $d_3$. While the larger proximal diameter $d_4$ is not necessary and the sleeve 16 can include an inner lumen 16c having a uniform inner diameter between the proximal and distal ends thereof, the larger proximal diameter $d_4$ allows the hollow sleeve 16 to optionally include a biasing member disposed therein for biasing the sleeve 16 with respect to the elongate shaft 12.

Virtually any biasing member can be used with the surgical drill guide assembly 10 of the present invention, however the biasing member should be effective to bias the elongate shaft 12 in a proximal direction such that a force greater than a biasing force created by the biasing member is required to move the elongate shaft in a distal direction with respect to the elongate, hollow sleeve 16. This will allow the sleeve 16 to be positioned within a lumen in a drill guide device without interference from the elongate shaft 12 since the biasing member will retain the shaft 12 at a particular position with respect to the hollow sleeve 16. In other words, the bone preparation element 14 will preferably not come into contact with bone during insertion of the device 10 into a guide lumen. In an exemplary embodiment, the biasing member is effective to position the distal end 12b of the elongate shaft 12 within or at least adjacent to the distal portion 16b of the hollow sleeve 16 when the biasing member is in the resting position. Thus, the sleeve 16 can be disposed within a lumen in a guide device, and a force can then be used to overcome the biasing force to cause the elongate shaft to move in a distal direction with respect to the sleeve 16, thereby inserting the bone preparation element 14 into bone.

Figure 5A:
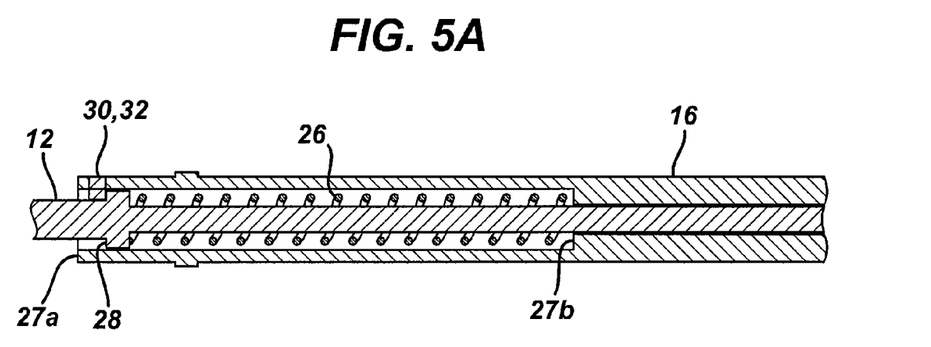
FIG. 5A is a cross-sectional view of a biasing member disposed within a portion of the sleeve of the surgical drill assembly shown in FIG. 1.

FIGS. 2 and 5A illustrate an exemplary embodiment of a biasing member 26, e.g., a spring, that is disposed within the proximal portion $16c_1$ of the inner lumen 16c of the sleeve 16. The biasing member 26 preferably has a size and shape that allow it to slidably receive the elongate shaft 12, and that allows it to extend between an open end 27a of the proximal portion 16a of the sleeve 16 and a surface or stepped region 27b formed between the proximal and distal portions $16c_1$, $16c_2$ in the inner lumen 16c of the sleeve 16. A flange 28 (FIGS. 3A and 5A) can be formed around a portion of the elongate shaft 12 and it can be positioned within the open end 27a of the sleeve 16 to receive the biasing force from the biasing member 26. The sleeve 16 can also include a pin 30 that is disposed through a pin bore 32 that is formed in the sleeve 16 adjacent to the open proximal end 27a. The pin 30, which is positioned just proximal to the flange 28 when the biasing member is in the resting position, is effective to retain the elongate shaft 12 within sleeve 16.

In use, the bone preparation element 14 is preferably disposed within or at least adjacent to the distal portion 16b of the hollow sleeve 16 when the biasing member 26 is in the resting position. As previously indicated, this allows the distal portion 16b of the sleeve to be disposed within a lumen in a guide device without the bone preparation element 14 coming into contact with bone. A force can then be applied to the elongate shaft 12, preferably by applying a force to a driver mechanism that is attached to the shaft 12, to move the shaft 12 in a distal direction. The force, if sufficient, will cause the biasing member 26 to be compressed between the flange 28 and the surface or stepped region 27b within the inner lumen 16c of the sleeve 16, and it will cause the bone preparation element 14 to extend distally from the sleeve 16. A person skilled in the art will appreciate that a variety of other techniques can be used to bias the elongate shaft 12 with respect to the hollow sleeve 16, and that FIGS. 2 and 5A merely illustrate an exemplary embodiment. Moreover, a variety of other techniques, other than a biasing member 26, can be used to maintain the position of the sleeve 16 with respect to the shaft 12, at least prior to advancing the shaft 12 into bone.

Figure 5B:
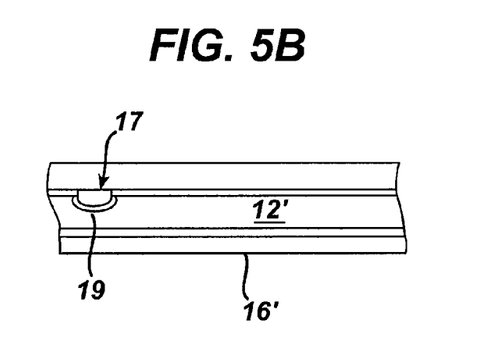
FIG. 5B is a cross-sectional view of a portion of another embodiment of a sleeve and shaft having an engagement element disposed therebetween for use with a surgical drill assembly according to the present invention.

By way of non-limiting example, FIG. 5B illustrates a portion of a shaft 12' and a sleeve 16' having a ball 17 and detent 19 disposed therein. The ball 17 preferably includes a spring-type mechanism that allows the ball 17 to be depressed into the sleeve 16' to allow the sleeve 16' to slide with respect to the shaft 12'. While the ball 17 is shown to be formed on the sleeve 16' and the detent 19 is shown to be formed on the shaft 12', the ball 17 can be formed on the shaft 12' and the detent 19 can be formed on the sleeve 16'. In use, the ball 17 and detent 19 are effective to at least temporarily maintain the position of the sleeve 16' around the shaft 12'. Once the sleeve 16' is disposed within a guide lumen, a force can be applied to the shaft 12' to disengage the ball 17 and detent 19, thereby allowing the shaft 12' to be advanced in a distal direction with respect to the sleeve 16'.

The surgical drill assembly of the present invention can also optionally include a stop member 20 that is effective to limit the penetration depth of the elongate shaft 12. As shown in FIGS. 1 and 2, and in more detail in FIG. 6, the stop member 20 is preferably disposed around a proximal portion of the elongate shaft 12 and it is effective to abut the proximal end 27a of the hollow sleeve 16 once the elongate shaft 12 has been moved a predetermined distance in a distal direction. The stop member 20 itself can have a variety of configurations, and it can be fixedly or adjustably attached to the elongate shaft 12. In the illustrated embodiment, however, the stop member 20 is a generally hollow, cylindrical tube that is slidably disposed around the shaft 12 and that is adjustable between several fixed positions along a length of the elongate shaft 12. The outer surface of the stop member 20 can optionally be knurled to facilitate gripping thereof.

Figure 6:
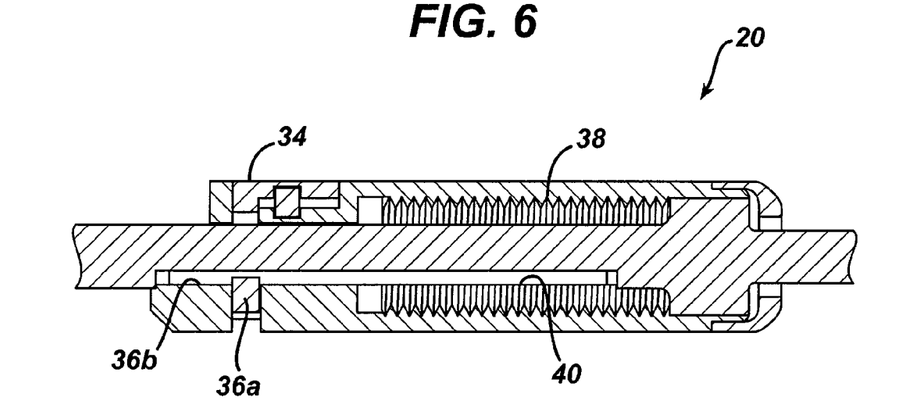
FIG. 6 is a cross-sectional view of one embodiment of a stop member disposed around a portion of the elongate shaft of the surgical drill assembly shown in FIG. 1.

A variety of techniques can be used to adjust the position of the stop member 20 on the elongate shaft 12. In the illustrated embodiment, a push-button mechanism 34 is coupled to pawl-and-ratchet mechanism 36a, 36b for adjusting the position of the stop member 20 along the length of the elongate shaft 12, and thereby allowing the penetration depth of the shaft 12 to be adjusted. The push-button mechanism 34 can be actuated to disengage the pawl 36a with the ratchet teeth 36b to relocate the position of the stop member 20. When the push-button 34 is released, the pawl 36a re-engages the ratchet teeth 36b and maintains the position of the stop member 20 on the elongate shaft 12. A person skilled in the art will appreciate that a variety of other techniques can be used to provide an adjustable stop member 20, and that the stop member 20 can have a variety of other configurations. Moreover, the stop member 20 can be used with a variety of other devices, and it is not limited to use with the elongate shaft 12 and/or sleeve 16 described herein.

Still referring to FIG. 6, the stop member 20 can also optionally or alternatively include threads 38 formed therein for mating with corresponding threads 40 (FIG. 3A) formed on the shaft 12. The threads 38, 40, when combined with the bush-button mechanism 34, will help maintain the position of the stop member 20 on the shaft 12 in the event that the push-button mechanism 34 is accidentally actuated during use of the device 10. In order to adjust the position of the stop member 20 along the shaft 12, the stop member 20 is rotated, rather than slid, when the push-button mechanism 34 is actuated. In an exemplary embodiment, the threads 38, 40 have a pitch that corresponds to the adjustment increment, such that one 360° rotation of the stop member 20 is effective to move the stop member 20 a predetermined distance along the shaft 12.

Figure 7A:
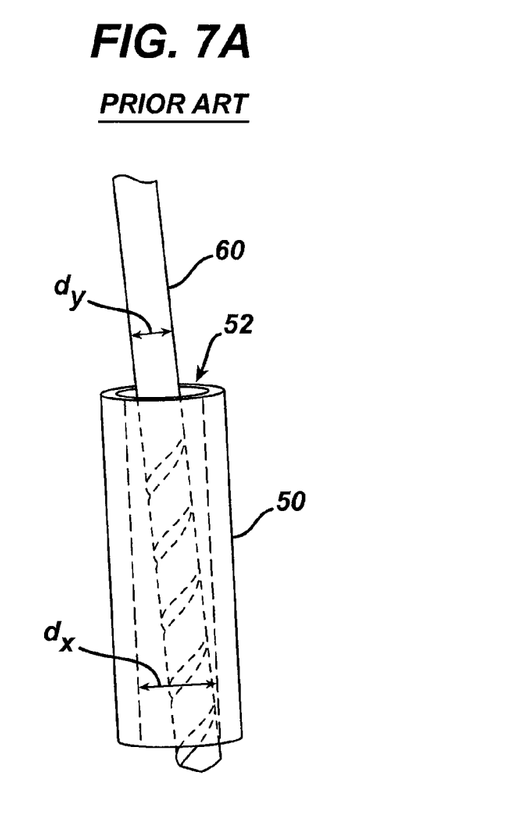
FIG. 7A is a partially transparent cross-sectional view of a prior art drill shaft disposed within a lumen of a prior art guide tube.
Figure 7B:
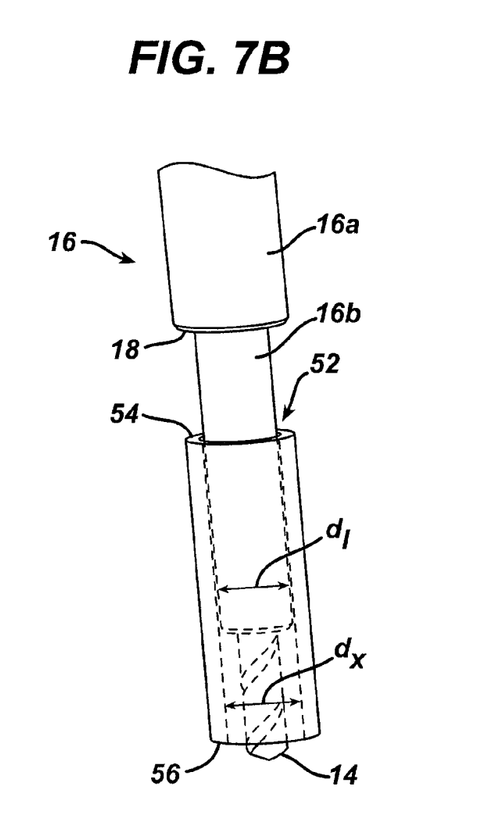
FIG. 7B is a is a partially transparent cross-sectional view of the surgical drill assembly shown in FIG. 1 disposed within a lumen of a prior art guide tube.

FIGS. 7A and 7B illustrate some advantages of using the surgical drill guide device 10 of the present invention over the prior art technique. As shown, FIG. 7A illustrates a prior art drill guide tube 50 and an elongate shaft, e.g., a drill bit 60, disposed through the guide tube 50. The drill guide tube 50 has an inner lumen 52 with a diameter $d_x$ that is significantly larger than a diameter $d_y$ of the drill bit 60. The large diameter $d_x$ is necessary in order to allow a fastening element, such as a spinal screw, to be inserted therethrough. As a result of the relatively large diameter $d_x$, the drill bit 60 is not centered within the guide tube 50, and thus the entry angle of the drill bit 60 can not be accurately controlled. Conversely, as shown in FIG. 7B, the sleeve 16 of the present invention is effective to center the elongate shaft 12 with respect to the guide tube 50, thereby providing precise control over the entry angle of the elongate shaft 12 into bone. More particularly, the distal portion 16b of the sleeve 16 can be inserted into the lumen 52 in the guide tube 50 such that a clearance fit, such as a sliding fit as previously described with respect to shaft 12 and sleeve 16, is provided therebetween. While FIG. 7B only illustrates the sleeve 16 partially inserted into the guide tube 50, the stepped region 18 between the proximal and distal portions 16a, 16b of the sleeve 16 can abut the proximal end surface 54 of the guide tube 50 to prevent the distal portion 16b of the sleeve 16 from extending distally beyond the distal end 56 of the guide tube 50. Once the sleeve 16 is positioned within the guide tube 50, the elongate shaft 12 can be advanced distally into bone to prepare the bone for a fastening element, or other implant. The sleeve 16 and shaft 12 can then be removed from the guide tube 50, thereby allowing a fastening device or other implant to be inserted through the guide tube 50.

A person skilled in the art will appreciate that the surgical drill assembly 10 of the present invention can be used with virtually any drill guide devices, and it is not limited to use with the particular device illustrated in FIG. 7B.

Figure 8:
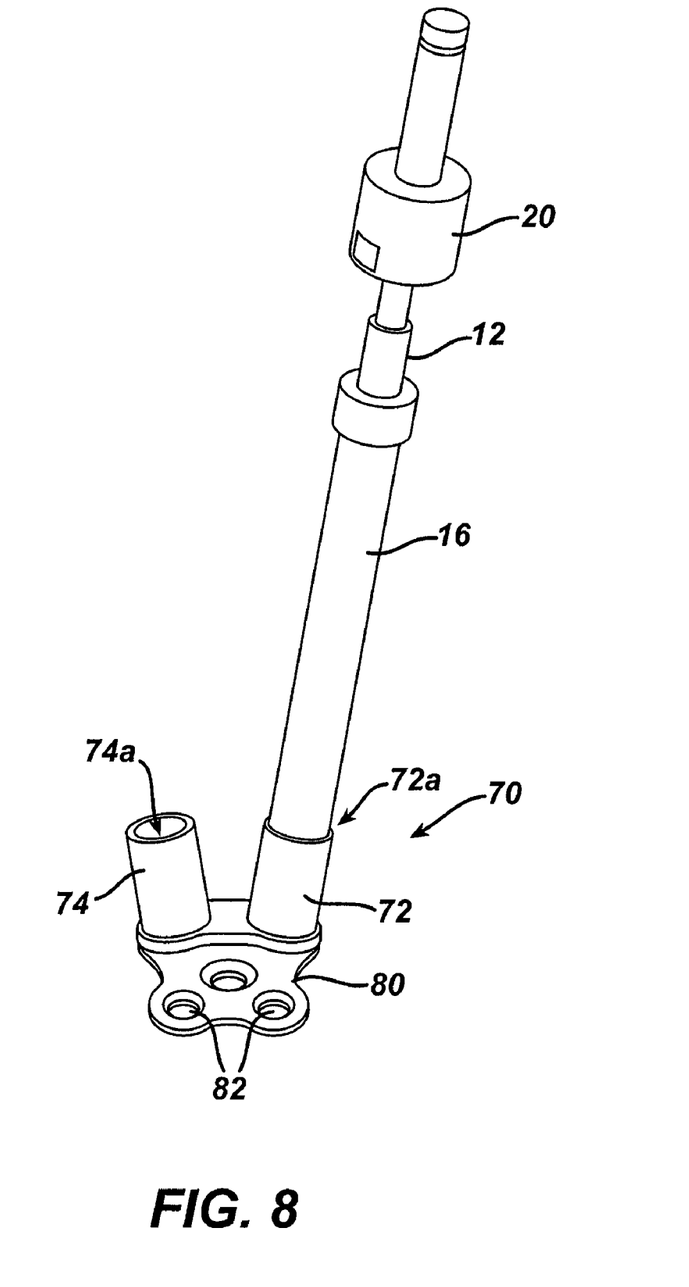
FIG. 8 is a perspective view of the surgical drill assembly of FIG. 1 coupled to a prior art guide device that is disposed on a prior art spinal fixation plate.

In another embodiment of a present invention, the surgical drill assembly 10 can be provided as part of a kit that includes a drill guide device, and that optionally includes one or more spinal fixation plates and/or one or more fastening elements. FIG. 8 illustrates one embodiment of a kit that includes the surgical drill assembly 10, a guide device 70 having first and second guide tubes 72, 74 with lumens 72a, 74a formed therein, and a spinal fixation plate 80 having two pairs of screw bores 82 (one pair is positioned under the guide device 70) formed therein and positioned on opposed ends of the plate 80. As shown, the guide tubes 72, 74 are aligned with a pair of screw bores (not shown) formed in the spinal fixation plate 80, and the distal portion (not shown) of the sleeve 16 is disposed within the lumen of one of the guide tubes, e.g., guide tube 72. The elongate shaft 12 can then be connected to a driver mechanism and advanced in a distal direction to cause the bone preparation element (not shown) formed on the distal end of the shaft 12 to advance through the screw bore in the spinal fixation plate 80 and into bone positioned adjacent to the plate 80, thereby preparing the bone. The surgical drill assembly 10 can then be removed from the guide device 70, and a fastening element or other implant can be inserted through the guide tube 72 in the guide device 70, or alternatively the guide device 70 can be removed from the plate 80 and then the fastening element or other implant can be disposed through the screw bore in the plate 80 and into bone. A variety of fastening elements, such as spinal screws, are known in the art and can be used with the present invention. While not illustrated, the kit can also include a variety of other tools that are effective to facilitate in the implantation of a spinal fixation plate.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical drill assembly, comprising:
   an elongate shaft having a proximal end adapted to mate to a driver mechanism, and a distal end having a bone preparation element formed thereon; and
   an elongate, hollow sleeve slidably disposed around at least a portion of the elongate shaft, the sleeve including a stepped region positioned between proximal and distal portions such that the distal portion has an outer diameter that is less than an outer diameter of the stepped region to allow the distal portion to be disposed within a lumen in a drill guide, and the stepped region to abut the drill guide;
   an engagement member formed on and disposed between the elongate shaft and the hollow sleeve such that the engagement is effective to temporarily maintain the hollow sleeve in a predetermined position with respect to the elongate shaft; and
   a stop member disposed around a proximal portion of the elongate shaft and adjustable to mate to the elongate shaft at a plurality of predetermined fixed positions along a length of the elongate shaft, the stop member being effective to abut the hollow sleeve to limit penetration of the distal end of the elongate shaft into bone;
   wherein the elongate, hollow sleeve is effective to longitudinally align the elongate shaft therein during a surgical procedure.

2. The surgical drill assembly of claim 1, wherein the elongate shaft is biased with respect to the elongate, hollow sleeve such that a force is necessary to overcome a biasing force to cause the elongate shaft to move in a distal direction with respect to the elongate, hollow sleeve.

3. The surgical drill assembly of claim 2, further comprising a biasing member disposed within at least a portion of the elongate, hollow sleeve to bias the elongate shaft in a proximal direction such that a force greater than a biasing force created by the biasing member is required to move the elongate shaft in a distal direction with respect to the elongate, hollow sleeve.

4. The surgical drill assembly of claim 3, wherein the biasing member comprises a spring.

5. The surgical drill assembly of claim 3, wherein the elongate shaft includes a flange formed therearound that is adapted to abut the biasing member.

6. The surgical drill assembly of claim 5, further comprising a pin extending through a sidewall of the hollow sleeve and adapted to abut the flange to prevent removal of the elongate shaft from within the hollow sleeve.

7. The surgical drill assembly of claim 1, wherein the engagement member comprises a ball and detent.

8. The surgical drill assembly of claim 1, wherein the stop member includes a distal surface that acts on a proximal surface of the hollow sleeve to limit penetration of the distal end of the elongate shaft into bone.

9. The surgical drill assembly of claim 8, wherein the stop member comprises a hollow tube that is disposed around the elongate shaft.

10. The surgical drill assembly of claim 9, further comprising a push-button mechanism coupled to the stop member that is effective to engage one of a plurality of detents formed in the elongate shaft to allow the position of the stop member along the length of the elongate shaft to be adjusted.

11. The surgical drill assembly of claim 9, wherein an inner surface of the hollow tube is threaded to mate with corresponding threads formed around at least a portion of the elongate shaft.

12. The surgical drill assembly of claim 11, further comprising a push-button mechanism coupled to the stop member that is effective to engage the elongate shaft to allow the position of the stop member along the length of the elongate shaft to be adjusted.

13. A surgical drill guide kit, comprising:
   a spinal fixation plate having at least one bore formed therein, and at least one fastening element adapted to be disposed through the bore in the spinal fixation plate;
   a drill guide member having at least one lumen formed therein and adapted to align with the at least one bore formed in the spinal fixation plate;
   an elongate shaft having a proximal end adapted to mate to a driver mechanism, and a distal end having a bone preparation element formed thereon; and
   an elongate, hollow sleeve disposed around at least a portion of the elongate shaft, the sleeve including a distal portion that is adapted to fit within the at least one lumen in the drill guide member, and a proximal portion having at least a region with an outer diameter that is larger than an inner diameter of the at least one lumen;
   wherein the elongate, hollow sleeve is effective to longitudinally align the elongate shaft with the at least one lumen in the drill guide member and with the at least one bore formed in the spinal fixation plate during a surgical procedure; and
   wherein the elongate shaft is biased with respect to the elongate, hollow sleeve such that a force is necessary to overcome a biasing force to cause the elongate shaft to move distally with respect to the elongate, hollow sleeve.

14. The surgical drill guide kit of claim 13, wherein the distal tip of the elongate shaft is disposed within a distal end of the elongate, hollow sleeve when the elongate shaft is in a resting position with respect to the elongate, hollow sleeve.

15. The surgical drill guide kit of claim 13, further comprising a biasing member disposed within at least a portion of the elongate, hollow sleeve to bias the elongate shaft in a proximal direction such that a force greater than a biasing force created by the biasing member is required to move the elongate shaft in a distal direction with respect to the elongate, hollow sleeve.

16. The surgical drill guide kit of claim 15, wherein the biasing member comprises a spring.

17. The surgical drill guide kit of claim 15, wherein the elongate shaft includes a flange formed therearound that is adapted to abut the biasing member.

18. The surgical drill guide kit of claim 13, further comprising a stop member disposed around a proximal portion of the elongate shaft that is effective to limit penetration of the distal end of the elongate shaft into bone.

19. The surgical drill guide kit of claim 18, wherein the stop member includes a distal surface that acts on a proximal surface of the hollow sleeve to limit penetration of the distal end of the elongate shaft into bone.

20. The surgical drill guide kit of claim 19, wherein the stop member comprises a hollow tube that is disposed around the elongate shaft, and that is slidably adjustable between a plurality of fixed positions along a length of the elongate shaft.

21. The surgical drill guide kit of claim 20, further comprising a push-button mechanism coupled to the stop member that is effective to engage one of a plurality of detents formed in the elongate shaft to allow the position of the stop member along the length of the elongate shaft to be adjusted.

22. The surgical drill guide kit of claim 20, an inner surface of the hollow tube is threaded to mate with corresponding threads formed around at least a portion of the elongate shaft.

23. The surgical drill guide kit of claim 20, further comprising a push-button mechanism coupled to the stop member that is effective to engage the elongate shaft to allow the position of the stop member along the length of the elongate shaft to be adjusted.

24. The surgical drill guide kit of claim 13, wherein the at least one fastening element includes a proximal head and a distal, bone engaging portion, the proximal head having a diameter that is less than an inner diameter of the at least one lumen in the drill guide member, and that is greater than an inner diameter of the hollow, elongate sleeve.

25. A surgical drill guide kit, comprising:

a drill guide member having at least one lumen formed therein and adapted to align with at least one corresponding bore formed in a spinal fixation plate;

an elongate shaft having a proximal end adapted to mate to a driver mechanism, and a distal end having a bone preparation element formed thereon; and an elongate, hollow sleeve disposed around at least a portion of the elongate shaft, the sleeve including a distal portion that is adapted to fit within the at least one lumen in the drill guide member, and a proximal portion having at least a region with an outer diameter that is larger than an inner diameter of the at least one lumen;

wherein the elongate, hollow sleeve is effective to longitudinally align the elongate shaft with the at least one lumen in the drill guide member and with at least one corresponding bore formed in a spinal fixation plate during a surgical procedure;

wherein the elongate shaft is biased with respect to the elongate, hollow sleeve such that a force is necessary to overcome a biasing force to cause the elongate shaft to move distally with respect to the elongate, hollow sleeve; and wherein the at least one lumen in the drill guide member has a length that is substantially the same as a length of the distal portion of the hollow, elongate sleeve.

* * * * *